United States Patent
Krapchetov et al.

(10) Patent No.: US 10,829,435 B2
(45) Date of Patent: *Nov. 10, 2020

(54) METHOD FOR PRODUCTION OF METHYL METHACRYLATE BY OXIDATIVE ESTERIFICATION USING A HETEROGENEOUS CATALYST

(71) Applicants: Dow Global Technologies LLC, Midland, MI (US); Rohm and Haas Company, Collegeville, PA (US)

(72) Inventors: Dmitry A. Krapchetov, Lansdale, PA (US); James Elder, Friendswood, TX (US); William G. Worley, Missouri City, TX (US); Kirk W. Limbach, Dresher, PA (US); Daniel A. Hickman, Midland, MI (US); Alexey Kirilin, Terneuzen (NL); Wen Sheng Lee, Midland, MI (US); Victor Sussman, Midland, MI (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/632,560

(22) PCT Filed: Jun. 25, 2018

(86) PCT No.: PCT/US2018/039242
§ 371 (c)(1),
(2) Date: Jan. 21, 2020

(87) PCT Pub. No.: WO2019/022892
PCT Pub. Date: Jan. 31, 2019

(65) Prior Publication Data
US 2020/0157036 A1  May 21, 2020

Related U.S. Application Data

(60) Provisional application No. 62/538,249, filed on Jul. 28, 2017.

(51) Int. Cl.
| C07C 67/44 | (2006.01) |
| B01J 21/04 | (2006.01) |
| B01J 21/06 | (2006.01) |
| B01J 23/52 | (2006.01) |
| B01J 35/00 | (2006.01) |
| B01J 35/02 | (2006.01) |
| B01J 35/08 | (2006.01) |
| B01J 37/02 | (2006.01) |

(52) U.S. Cl.
CPC .............. *C07C 67/44* (2013.01); *B01J 21/04* (2013.01); *B01J 21/063* (2013.01); *B01J 23/52* (2013.01); *B01J 35/008* (2013.01); *B01J 35/023* (2013.01); *B01J 35/08* (2013.01); *B01J 37/0219* (2013.01); *B01J 37/0221* (2013.01)

(58) Field of Classification Search
CPC ......... C07C 67/39; C07C 45/75; C07C 69/54; B01J 23/89; B01J 23/44
See application file for complete search history.

(56) References Cited

U.S. PATENT DOCUMENTS

| 4,249,019 A | 2/1981 | Tamura et al. |
| 4,518,796 A | 5/1985 | Aoshima et al. |
| 4,520,125 A | 5/1985 | Baer et al. |
| 5,892,101 A | 4/1999 | Brookhart et al. |
| 5,969,178 A | 10/1999 | Okamoto et al. |
| 6,040,472 A | 3/2000 | Yamamatsu et al. |
| 6,107,515 A | 8/2000 | Yamaguchi et al. |
| 6,228,800 B1 | 5/2001 | Yamaguchi et al. |
| 7,326,806 B2 | 2/2008 | Hayashi et al. |
| 8,461,373 B2 | 6/2013 | Suzuki et al. |
| 8,614,349 B2 | 12/2013 | Yokota et al. |
| 9,511,351 B2 | 12/2016 | Feaviour |
| 9,617,199 B2 | 4/2017 | Krill et al. |
| 2016/0068464 A1 | 3/2016 | Krill et al. |
| 2016/0251301 A1 | 9/2016 | Krill et al. |
| 2016/0280628 A1 | 9/2016 | Krill et al. |

FOREIGN PATENT DOCUMENTS

| CN | 1931824 A | 3/2007 |
| JP | 2003048863 A | 2/2003 |
| WO | 2017084969 | 5/2017 |

*Primary Examiner* — Jafar F Parsa
(74) *Attorney, Agent, or Firm* — Brian L. Mutschler

(57) ABSTRACT

A method for preparing methyl methacrylate from methacrolein and methanol; said method comprising contacting in a reactor a mixture comprising methacrolein, methanol and oxygen with a heterogeneous catalyst comprising a support and a noble metal, wherein pH at the reactor outlet is from 3 to 6.7.

10 Claims, No Drawings

METHOD FOR PRODUCTION OF METHYL METHACRYLATE BY OXIDATIVE ESTERIFICATION USING A HETEROGENEOUS CATALYST

BACKGROUND OF THE INVENTION

The invention relates to a method for preparing methyl methacrylate from methacrolein and methanol using a heterogeneous catalyst.

Methyl methacrylate has been produced by oxidative esterification reactions in which decreases in pH of the reaction mixture are known to be detrimental. The prior art teaches addition of base to the reactor to raise pH to extend catalyst life which otherwise would be shortened under acidic conditions. The solution to this problem has been to mix the base into a portion of the reaction mixture in a separate vessel, see, e.g., U.S. Pub. No. 2016/0251301. However, there is a need for a more efficient process which can provide high space-time yield, improved selectivity and reduced costs.

SUMMARY OF THE INVENTION

The present invention is directed to a method for preparing methyl methacrylate from methacrolein and methanol; said method comprising contacting in a reactor a mixture comprising methacrolein, methanol and oxygen with a heterogeneous catalyst comprising a support and a noble metal, wherein pH at the reactor outlet is from 3 to 6.7.

DETAILED DESCRIPTION OF THE INVENTION

All percentage compositions are weight percentages (wt %), and all temperatures are in ° C., unless otherwise indicated. Averages are arithmetic averages unless otherwise indicated. A noble metal is any of gold, platinum, iridium, osmium, silver, palladium, rhodium and ruthenium. More than one noble metal may be present in the catalyst, in which case the limits apply to the total of all noble metals. The "catalyst center" is the centroid of the catalyst particle, i.e., the mean position of all points in all coordinate directions. A diameter is any linear dimension passing through the catalyst center and the average diameter is the arithmetic mean of all possible diameters. The aspect ratio is the ratio of the longest to the shortest diameters.

Preferably, pH at the reactor outlet is at least 3.5, preferably at least 4, preferably at least 4.5, preferably at least 4.8, preferably at least 5; preferably no more than 6.6, preferably no more than 6.5, preferably no more than 6.4, preferably no more than 6.3, preferably no more than 6.2. Preferably, base is not added to the reactor or to liquid streams entering the reactor. Preferably, the reactor is not connected to an external mixing tank through which base is introduced. pH in the reactor is likely to be higher, possibly above 7 near the inlet and dropping below 6 at the outlet. Preferably, pH at the inlet is no greater than 8, preferably no greater than 7.5, preferably no greater than 7.

Preferably, the support is a particle of a refractory oxide; preferably γ-, δ-, or θ-alumina, silica, magnesia, titania, zirconia, hafnia, vanadia, niobium oxide, tantalum oxide, ceria, yttria, lanthanum oxide or a combination thereof; preferably titania or γ-, δ-, or θ-alumina. Preferably, in portions of the catalyst comprising the noble metal, the support has a surface area greater than 10 m$^2$/g, preferably greater than 30 m$^2$/g, preferably greater than 50 m$^2$/g, preferably greater than 100 m$^2$/g, preferably greater than 120 m$^2$/g. In portions of the catalyst which comprise little or no noble metal, the support may have a surface area less than 50 m$^2$/g, preferably less than 20 m$^2$/g.

Preferably, the aspect ratio of the catalyst particle is no more than 10:1, preferably no more than 5:1, preferably no more than 3:1, preferably no more than 2:1, preferably no more than 1.5:1, preferably no more than 1.1:1. Preferred shapes for the catalyst particle include spheres, cylinders, rectangular solids, rings, multi-lobed shapes (e.g., cloverleaf cross section), shapes having multiple holes and "wagon wheels;" preferably spheres. Irregular shapes may also be used.

Preferably, at least 90 wt % of the noble metal(s) is in the outer 70% of catalyst volume (i.e., the volume of an average catalyst particle), preferably the outer 60% of catalyst volume, preferably the outer 50%, preferably the outer 40%, preferably the outer 35%, preferably in the outer 30%, preferably in the outer 25%. Preferably, the outer volume of any particle shape is calculated for a volume having a constant distance from its inner surface to its outer surface (the surface of the particle), measured along a line perpendicular to the outer surface. For example, for a spherical particle the outer x % of volume is a spherical shell whose outer surface is the surface of the particle and whose volume is x % of the volume of the entire sphere. Preferably, at least 95 wt % of the noble metal is in the outer volume of the catalyst, preferably at least 97 wt %, preferably at least 99 wt %. Preferably, at least 90 wt % (preferably at least 95 wt %, preferably at least 97 wt %, preferably at least 99 wt %) of the noble metal(s) is within a distance from the surface that is no more than 30% of the catalyst diameter, preferably no more than 25%, preferably no more than 20%, preferably no more than 15%, preferably no more than 10%, preferably no more than 8%. Distance from the surface is measured along a line which is perpendicular to the surface.

Preferably, the noble metal is gold or palladium, preferably gold.

Preferably, the average diameter of the catalyst particle is at least 60 microns, preferably at least 100 microns, preferably at least 200 microns, preferably at least 300 microns, preferably at least 400 microns, preferably at least 500 microns, preferably at least 600 microns, preferably at least 700 microns, preferably at least 800 microns; preferably no more than 30 mm, preferably no more than 20 mm, preferably no more than 10 mm, preferably no more than 5 mm, preferably no more than 4 mm. The average diameter of the support and the average diameter of the final catalyst particle are not significantly different.

Preferably, the amount of noble metal as a percentage of the noble metal and the support is from 0.2 to 5 wt %, preferably at least 0.5 wt %, preferably at least 0.8 wt %, preferably at least 1 wt %, preferably at least 1.2 wt %; preferably no more than 4 wt %, preferably no more than 3 wt %, preferably no more than 2.5 wt %.

Preferably, the catalyst is produced by precipitating the noble metal from an aqueous solution of metal salts in the presence of the support. In one preferred embodiment, the catalyst is produced by an incipient wetness technique in which an aqueous solution of a suitable noble metal precursor salt is added to a porous inorganic oxide such that the pores are filled with the solution and the water is then removed by drying. The resulting material is then converted into a finished catalyst by calcination, reduction, or other pre-treatments known to those skilled in the art to decompose the noble metal salts into metals or metal oxides. Preferably, a $C_2$-$C_{18}$ thiol comprising at least one hydroxyl or carboxylic acid substituent is present in the solution. Preferably, the $C_2-C_{18}$ thiol comprising at least one hydroxyl or carboxylic acid substituent has from 2 to 12 carbon atoms, preferably 2 to 8, preferably 3 to 6. Preferably, the thiol compound comprises no more than 4 total hydroxyl and carboxylic acid groups, preferably no more than 3, preferably no more than 2. Preferably, the thiol compound has no more than 2 thiol groups, preferably no more than one. If the thiol compound comprises carboxylic acid substituents, they may be present in the acid form, conjugate base form or a mixture thereof. Especially preferred thiol compounds include thiomalic acid, 3-mercaptopropionic acid, thioglycolic acid, 2-mercaptoethanol and 1-thioglycerol, including their conjugate bases.

In one embodiment of the invention, the catalyst is produced by deposition precipitation in which a porous inorganic oxide is immersed in an aqueous solution containing a suitable noble metal precursor salt and that salt is then made to interact with the surface of the inorganic oxide by adjusting the pH of the solution. The resulting treated solid is then recovered (e.g. by filtration) and then converted into a finished catalyst by calcination, reduction, or other pre-treatments known to those skilled in the art to decompose the noble metal salts into metals or metal oxides.

Preferably, the process for producing methyl methacrylate (MMA) is performed in an oxidative esterification reactor (OER). The catalyst particles may be present in a slurry or in a catalyst bed, preferably a catalyst bed. The catalyst particles in the catalyst bed typically are held in place by solid walls and by screens or catalyst support grids. In some configurations, the screens or grids are on opposite ends of the catalyst bed and the solid walls are on the side(s), although in some configurations the catalyst bed may be enclosed entirely by screens. Preferred shapes for the catalyst bed include a cylinder, a rectangular solid and a cylindrical shell; preferably a cylinder. The OER further comprises a liquid phase comprising methacrolein, methanol and MMA and a gaseous phase comprising oxygen. The liquid phase may further comprise byproducts, e.g., methacrolein dimethyl acetal (MDA) and methyl isobutyrate (MIB). Preferably, the liquid phase is at a temperature from 40 to 120° C.; preferably at least 50° C., preferably at least 60° C.; preferably no more than 110° C., preferably no more than 100° C. Preferably, the catalyst bed is at a pressure from 0 to 2000 psig (101 kPa to 14 MPa); preferably no more than 2000 kPa, preferably no more than 1500 kPa.

The OER typically produces MMA, along with methacrylic acid and unreacted methanol. Preferably, methanol and methacrolein are fed to the reactor in a methanol:methacrolein molar ratio from 1:10 to 100:1, preferably from 1:2 to 20:1, preferably from 1:1 to 10:1. Preferably, a catalyst bed further comprises inert materials above and/or below the catalyst. Preferred inert materials include, e.g., alumina, clay, glass, silica carbide and quartz. Preferably, the inert material has an average diameter equal to or greater than that of the catalyst, preferably no greater than 20 mm. Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid, salts and water. MDA may be hydrolyzed in the bottoms stream from a methanol recovery distillation column; said stream comprising MMA, MDA, methacrylic acid, salts and water. In another embodiment, MDA is hydrolyzed in an organic phase separated from the methanol recovery bottoms stream.

It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts. In another embodiment, hydrolysis could be conducted within the distillation column itself.

One preferred embodiment is a recycle reactor with cooling capacity in the recycle loop. Another preferred embodiment is a series of reactors with cooling and mixing capacity between the reactors.

Preferably, oxygen concentration at a reactor outlet is at least 0.5 mole %, preferably at least 2 mole %, preferably at least 3 mole %; preferably no more than 7 mole %, preferably no more than 6.5 mole %, preferably no more than 6 mole %.

One preferred embodiment of the fixed bed reactor for oxidative esterification is a trickle bed reactor, which contains a fixed bed of catalyst and passes both the gas and liquid feeds through the reactor in the downward direction. In trickle flow, the gas phase is the continuous fluid phase. Thus, the zone at the top of the reactor, above the fixed bed, will be filled with a vapor phase mixture of nitrogen, oxygen, and the volatile liquid components at their respective vapor pressures. Under typical operating temperatures and pressures (50-90° C. and 60-300 psig), this vapor mixture is inside the flammable envelope if the gas feed is air. Thus, only an ignition source would be required to initiate a deflagration, which could lead to loss of primary containment and harm to the physical infrastructure and personnel in the vicinity. In order to address process safety considerations, a means to operate a trickle bed reactor while avoiding a flammable headspace atmosphere is operation with a gas feed containing a sufficiently low oxygen mole fraction to ensure the oxygen concentration in the vapor headspace is below the limiting oxygen concentration (LOC).

Knowledge of the LOC is required for the fuel mixture, temperature, and pressure of concern. Since the LOC decreases with increasing temperature and pressure, and given that methanol gives a lower LOC than the other two significant fuels (methacrolein and methyl methacrylate), a conservative design chooses a feed oxygen to nitrogen ratio that ensures a composition with less than the LOC at the highest expected operating temperature and pressure. For example, for a reactor operated at up to 100° C. and 275 psig, the feed oxygen concentration in nitrogen should not exceed 7.4 mol %.

EXAMPLES

Example #1

Feed consisting primarily of methacrolein, methanol and sometimes base were fed to a fixed bed reactor in order to produce MMA. The fixed bed reactor was operated as an adiabatic packed bubble column Air and liquid feed were fed into the bottom of the vertically aligned reactor (a 2-inch (51 mm) OD (1.624-inch (41.2 mm) ID)×108 inch (274 cm) insulated 316SS tube). The liquid feed was approximately 35 wt % methacrolein and was pumped from the feed mix tank to the suction of a positive displacement pump. The positive displacement pump recycles reactor product from the gas-liquid separation tank with make-up from the feed mix tank. Gas was introduced into the reactor using a frit located at the base of the reactor. The pH of the feed entering the reactor was measured. The liquid feed is pre-heated to the desired temperature using a heat exchanger. The reactor product is sent to the gas-liquid separation vessel, which is jacketed and cooled with cooling water. Base (25 wt % NaOH in water) is optionally pumped into the gas-liquid separation tank. The addition of base was designed to neutralize the methacrylic acid formed in the reactor. The target acid neutralization was 50 mol %, corresponding to a measured pH near 7. To maintain adequate mixing for acid-base neutralization, the gas-liquid separation tank was agitated, with impellers approximately equally separated in the liquid from top to bottom. Vapors from the gas-liquid separation tank passed through a condenser, where noncondensable gases exit through a vent. Oxygen concentration in the vented noncondensable stream is monitored using an online oxygen analyzer downstream of the condenser. A polymerization inhibitor is pumped into the top of the condenser, where it drips back into the gas-liquid separation tank. Inhibitor also enters with the feed.

Description of catalyst 1: The catalyst is 1.44+/−0.05 wt % Au (measured by NAA-ICP) on 1 mm high-surface-area $Al_2O_3$ spheres. The catalyst is produced by incipient wetness technique using Au thiomalate as a gold precursor, which has been shown to provide an eggshell loading of the Au around the 1 mm $Al_2O_3$ spheres.

Description of catalyst 2: The catalyst is approximately 1.5 wt % Au on 3.2 mm high-surface-area $Al_2O_3$ spheres. The catalyst is produced by incipient wetness technique using Au thiomalate as a gold precursor, which has been shown to provide an eggshell loading of the Au.

| Cat. | base | pH at FB inlet* | conv (%) | STY (mol MMA/ kg cat hr) | Prod. MMA (%) | MIB (ppm) | $P_{inlet}$ (psig) | $P_{outlet}$ (psig) | Air Rate, SLPM | Feed Rate (g/hr) | Feed + Recycle Rate (g/hr) | T outlet (C.) |
|---|---|---|---|---|---|---|---|---|---|---|---|---|
| 1 | Off | 5.7 | 54.60 | 4.5 | 97% | 280 | 281 | 276 | 9.7 | 2636 | 13256 | 78 |
| 1 | On | 7.0 | 66.70 | 5.0 | 98% | 227 | 280 | 275 | 11 | 2636 | 15877 | 80 |
| 2 | On | 6.7 | 58.20 | 3.4 | 97% | 507 | 164 | 161 | 7.5 | 1810 | 15813 | 70 |
| 2 | Off | 5.7 | 62 | 3.2 | 97% | 318 | 163 | 160 | 7.2 | 1767 | 15501 | 69 |

*Estimated from MAA content.

Notes:
1. Performance is similar with or without base. Prod MMA is the percent MMA among products originating as methacrolein reactant. MIB is on a 100% MMA basis.
2. Fouling of Downstream Separations Section:
When base was added, the column pressure drop kept increasing which made it difficult to continue operation of the downstream distillation column. In particular, for the catalyst 1 case, pressure drop in at least one column of the distillation section increased by 10% over the course of approximately 3 days which prohibited further operation. Analysis of residues in the column showed the presence of aluminum salts and solids appear to form more readily in the distillation section in the base addition case. In the absence of base, the downstream distillation operated without any pressure drop buildup.

Example #2

A series of runs was conducted in which 20 wt % methacrolein, 200 ppm inhibitor, and a balance of methanol were fed to a ⅜" stainless steel tubular reactor containing a short front section of silicon carbide followed by 10 g of catalyst. The catalyst consisted of 1.5 wt % Au on a Norpro 1 mm diameter high surface area alumina spherical support. Air or a gas containing 8 mol % oxygen in nitrogen were also feed to the reactor. The reactor was operated at 60° C. and 160 psig (1200 kPa). The product of the reactor was sent to a liquid-vapor separator and the vapor was sent to a condenser with liquid return. A portion of the product stream from this separator was recycled in some cases to the reactor inlet and combined with the feed entering the reactor. Results are described in the below table. MIB is reported in ppm on a 100% MMA product basis. Product MMA is the percent MMA among products originating as methacrolein reactant.

| Base type | Feed (g/hr) | recyc. (g/hr) | Base (g/hr) | pH out | Gas (sccm) | Gas Type | Prod MMA MMA, % | Conv (%) | STY (m/Kg hr) | MIB (ppm) |
|---|---|---|---|---|---|---|---|---|---|---|
| None | 20 | 0 | 0 | 5.7 | 450 | 8% O$_2$ | 97.8 | 76 | 3.8 | 460 |
| None | 20 | 180 | 0 | 5.7 | 380 | 8% O$_2$ | 97.8 | 63 | 3.2 | 480 |
| None | 200 | 0 | 0 | 6.3 | 190 | AIR | 97.9 | 15 | 8.2 | 600 |
| 0.15 wt % NaOMe | 20 | 180 | 20 | 6.8 | 300 | 8% O$_2$ | 93.7 | 60 | 2.7 | 800 |
| None | 100 | 0 | 0 | na | 120 | AIR | 97.5 | 29 | 6.5 | na |
| None | 150 | 0 | 0 | na | 120 | AIR | 97.2 | 21 | 6.8 | 220 |

Note:
Performance is similar with or without base.

The invention claimed is:

1. A method for preparing methyl methacrylate from methacrolein and methanol; said method comprising contacting in a reactor a mixture comprising methacrolein, methanol and oxygen with a heterogeneous catalyst comprising a support and gold, wherein pH at the reactor outlet is from 3 to 6.7, wherein the average diameter of particles of the heterogeneous catalyst is at least 300 microns and at least 90 wt % of the gold is in the outer 70% of catalyst volume.

2. The method of claim 1 in which at least 90 wt % of the gold is in the outer 60% of catalyst volume.

3. The method of claim 2 in which average diameter of particles of the heterogeneous catalyst is at least 400 microns.

4. The method of claim 3 in which the amount of gold as a percentage of the gold and the support is from 0.2 to 5 wt %.

5. The method of claim 4 in which temperature in the reactor is from 40 to 120° C.

6. The method of claim 5 in which at least 95 wt % of the gold is in the outer 50% of catalyst volume.

7. The method of claim 6 in which pH in the reactor is from 4.5 to 6.5.

8. The method of claim 1 in which the support is titania.

9. The method of claim 8 in which at least 90 wt % of the gold is in the outer 60% of catalyst volume.

10. The method of claim 9 in which average diameter of particles of the heterogeneous catalyst is at least 400 microns.

* * * * *